United States Patent [19]

Tsuji et al.

[11] Patent Number: 5,411,990
[45] Date of Patent: May 2, 1995

[54] INDUSTRIAL MICROBICIDE AND A METHOD FOR KILLING MICROBES FOR INDUSTRIAL USE

[75] Inventors: Katsuji Tsuji, Kyoto; Hidenori Hirashima, Osaka, both of Japan

[73] Assignees: Yoshitomi Pharmaceutical Industries Ltd.; Katayama Chemical Inc., both of Osaka, Japan

[21] Appl. No.: 62,661

[22] Filed: May 17, 1993

[30] Foreign Application Priority Data

May 18, 1992 [JP]  Japan .................................. 4-125105
May 22, 1992 [JP]  Japan .................................. 4-130929
Apr. 28, 1993 [JP]  Japan .................................. 5-103140

[51] Int. Cl.$^6$ .................. A01N 33/24; A01N 47/40; A01N 43/78; A01N 37/34
[52] U.S. Cl. ..................... 514/640; 514/516; 514/515; 514/372; 514/579; 514/626; 514/645; 514/709; 514/525
[58] Field of Search ............. 514/640, 516, 515, 372, 514/525, 579, 626, 645, 709

[56] References Cited

U.S. PATENT DOCUMENTS

| 4,661,517 | 4/1987 | Martin et al. | 514/515 |
| 5,131,939 | 7/1992 | Hsu | 514/640 |
| 5,273,987 | 12/1993 | Hsu | 514/515 |

FOREIGN PATENT DOCUMENTS

| 3-83902 | 4/1991 | Japan . |
| 3-167101 | 7/1991 | Japan . |
| 3-170404 | 7/1991 | Japan . |
| 5-105604 | 4/1993 | Japan . |
| 1307223 | 2/1973 | United Kingdom . |

OTHER PUBLICATIONS

DIRASAT, vol 13, No. 7, 1986, pp. 185–188, F. Khalili et al., "Preparation and Antimicrobial Activity of Glyoximes".

Primary Examiner—Allen J. Robinson
Assistant Examiner—Deborah Lambkin
Attorney, Agent, or Firm—Cohen, Pontani, Lieberman, Pavane

[57] ABSTRACT

An industrial microbicide which comprises at least one haloglyoxime derivative of the formula (I):

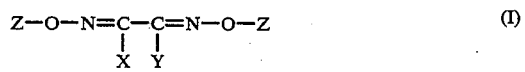

wherein X is a halogen atom; Y is a hydrogen atom, a halogen atom or a lower alkyl group having 1 to 4 carbon atoms; and Z is a hydrogen atom or an optionally halogenated lower alkanoyl group having 1 to 5 carbon atoms; and a known industrial microbicidal ingredient selected from the group consisting of an organonitrogen-sulfur compound, an organohalogen compound, an organonitrogen compound and an organosulfur compound; and optionally a carrier or diluent.

9 Claims, No Drawings

INDUSTRIAL MICROBICIDE AND A METHOD FOR KILLING MICROBES FOR INDUSTRIAL USE

BACKGROUND OF THE INVENTION

1. Field of the Invention

The present invention relates to an industrial microbicidal or microbistatic agent and a method of killing microbes or inhibiting the growth of microbes for industrial use. More particularly, it relates to an industrial microbicidal or microbistatic agent and also to a method of killing microbes or inhibiting the growth of microbes for industrial use which is effective for antiseptic, microbicidal or microbistatic treatment of water used in the paper manufacturing steps in paper and pulp industries; water for cooling and for washing in various industries; fuel oil sludge; metal working fluid; textile oil; paint; antifouling paint; coating color for paper; latex; adhesive; etc.

2. Description of the Prior Art

Slimes generated due to the growth of bacteria and/or fungi in cooling water and process water of the paper/pulp industry or various industries deteriorate a quality of products and efficiency of production. Further, in various industrial products, such as heavy oil sludges, cutting fluids, textile oils, paints, various latices and sizings, putrefaction and contamination occur due to the growth of bacteria and/or fungi which reduce their value.

For the prevention of such problems caused by microorganisms, many microbicides have been used. Previously, organomercury compounds and chlorinated phenols were used for this purpose. However, the use of these compounds is to be regulated, because they have a strong toxicity to the human body, fish and shellfish and may cause environmental pollution.

Lately, organonitrogen-sulfur compounds such as methylenebisthiocyanate, 1,2-benzoisothiazolin-3-one and 5-chloro-2-methyl-4-isothiazolin-3-one, organobromine compounds such as 2,2-dibromo-2-nitroethanol, 2,2-dibromo-3nitrilopropionamide, 1,2-bis(-bromoacetoxy)ethane, 1,4-bis(bromoacetoxy)-2-butene and bis(tribromomethyl)sulfone and organosulfur compounds such as 4,5-dichloro-1,2-dithiol-3-one which have relatively low toxicity, are practically used [see BOKIN-BOKABI-JITEN (Dictionary of Antibacterial and Antifungal Agent) published by The Society for Antibacterial and Antifungal Agents, Japan, 1986; Japanese Laid-Open Patent Publication Nos. (HEI) 3-170404/1991, 3-83902/1991 and 3-167101/1991].

It is reported that dichloroglyoxime can inhibit the growth of representative gram-negative and gram-positive bacteria, but its homologues such as glyoxime and dimethylglyoxime do not exert such inhibition (Dirasat, 13(7), 185-188(1986)).

However, it is not known that monohaloglyoxime shows more potent microbicidal property than dihaloglyoxime and the combination use of monohaloglyoxime and dihaloglyoxime and of such glyoxime derivatives and known industrial microbicides can expect synergistic microbicidal effects.

SUMMARY OF THE INVENTION

The present invention provides an industrial microbicide which comprises as an effective ingredient at least one haloglyoxime derivative of the formula (I'):

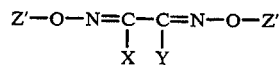

wherein X is a halogen atom; Y is a hydrogen atom, a halogen atom or a lower alkyl group having 1 to 4 carbon atoms; and Z' is a hydrogen atom or an optionally halogenated lower alkanoyl group having 1 to 5 carbon atoms; provided that Z' is an optionally halogenated lower alkanoyl group having 1 to 5 carbon atoms when Y is a halogen atom, and optionally a carrier or diluent.

The present invention also provides an industrial microbicide which comprises:

at least one haloglyoxime derivative of the formula (I):

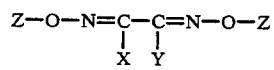

wherein X is a halogen atom; Y is a hydrogen atom, a halogen atom or a lower alkyl group having 1 to 4 carbon atoms; and Z is a hydrogen atom or an optionally halogenated lower alkanoyl group having 1 to 5 carbon atoms; and at least one known industrial microbicidal ingredient selected from the group consisting of an organonitrogen-sulfur compound, an organohalogen compound, an organonitrogen compound and an organosulfur compound, as an effective ingredient, and optionally a carrier or diluent.

Further, the present invention provides a method for killing microbes for industrial use by adding a microbicidally effective amount of a haloglyoxime derivative (I') to an industrial medium.

The present invention also provides a method for killing microbes for industrial use by adding a microbicidally effective amount of each of a haloglyoxime derivative (I) and a known industrial microbicidal ingredient simultaneously or separately to an industrial medium.

PREFERRED EMBODIMENT

The lower alkyl group having 1 to 4 carbon atoms represented by Y in the above formulae (I') and (I) includes methyl, ethyl, propyl, isopropyl, butyl, isobutyl, t-butyl, etc. Among those, methyl is preferred.

The lower alkanoyl group having 1 to 5 carbon atoms represented by Z' and Z in the above formulae (I') and (I) includes acetyl, propionyl, butyryl, isobutyryl, etc. Among The halogen atom represented by X and Y in the above formulae (I') and (I) includes chlorine, bromine, fluorine and iodine. Among those, chlorine is preferred. The halogen atom in the optionally halogenated lower alkanoyl group represented by Z' and Z is also defined as the same above.

Examples of the haloglyoxime derivatives shown by the above formulae (I') and (I) include monohaloglyoximes such as monochloroglyoxime, monobromoglyoxime, monofluoroglyoxime, monoiodoglyoxime, 1-chloro-2-methylglyoxime, 1-chloro-2-ethylglyoxime, 1-chloro-2-propylglyoxime, 1-chloro-2-butylglyoxime, 1-bromo-2-methylglyoxime, 1-bromo-2-ethylglyoxime, 1-bromo-2-propylglyoxime, 1-bromo-2-butylglyoxime, 1-fluoro-2-methylglyoxime, 1-fluoro-2-ethylglyoxime, 1-fluoro-2-propylglyoxime, 1-fluoro-2butylglyoxime, 1-iodo-2-methylglyoxime, 1-iodo-2-ethylglyoxime, 1-iodo-2-propylglyoxime, 1-iodo-2-butylglyoxime, etc; dihaloglyoxime such as dichloroglyoxime, dibromoglyoxime, difluoroglyoxime, diiodoglyoxime, etc; and dihaloglyoxime diacylates such as dichloroglyoxime diacetate, dichloroglyoxime dipropionate, dichloroglyoxime di-n-butyrate, dichloroglyoxime di-iso-butyrate, dichloroglyoxime bis(chloroacetate), etc. Among those, monochloroglyoxime, 1-chloro-2-methylglyoxime, dichloroglyoxime and dichloroglyoxime dipropionate are preferable.

The monohaloglyoximes as mentioned above can be easily synthesized by halogenation of glyoxime. The dihaloglyoximes can be obtained by further halogenation of the monohaloglyoxime.

The dihaloglyoxime diacylates can be synthesized by acylation of the dihaloglyoxime in accordance with a known method. For example, dihaloglyoxime diacylate can be prepared by reacting dihaloglyoxime with a carboxylic acid anhydride in the presence of an acidic catalyst, or with a carboxylic acid chloride in the presence of triethylamine.

The haloalkylglyoxime can be synthesized by reacting an alkylglyoxal with hydroxylamine to form alkylglyoxime and then halogenating the resulting alkylglyoxime.

The microbicide of the present invention can exhibit a significant microbicidal effect even in an industrial medium containing a reducing agent equal to or more than 5 mg/l in terms of sulfite ion.

Also, the present invention provides an industrial microbicide comprising the haloglyoxime derivative (I') or (I) and a known industrial microbicidal ingredient. The combined use would be effective in broadening antibacterial spectra and developing the additive or synergistic effect of antimicrobicidal activities.

The known industrial microbicidal ingredients include organonitrogen-sulfur compounds, organohalogen compounds, organonitrogen compounds and organosulfur compounds.

Examples of the organonitrogen-sulfur compounds include alkylenebisthiocyanates such as methylenebisthiocyanate and ethylenebisthiocyanate; 3-isothiazolone compounds and complexes thereof such as 5-chloro-2-methyl-4-isothiazolin-3-one, 2-methyl-4-isothiazolin-3-one, 4,5-dichloro-2-n-octyl-isothiazolin-3-one and 2-n-octyl-isothiazolin-3-one and complexes thereof with magnesium chloride or calcium chloride; dithiocarbamates such as ammonium N-methyldithiocarbamate, sodium N-methyldithiocarbamate, sodium dimethyldithiocarbamate, ethylenethiuram monosulfide, disodium ethylenebis(dithiocarbamate) and manganese ethylenebisdithiocarbamate; sulfonamides such as chloramine T and N,N-dimethyl-N'-(fluorodichloromethylthio)-N'-phenylsulfamide; thiazole compounds such as 2(thiocyanomethylthio)benzothiazole and sodium 2-mercaptobenzothiazole; s-triazine compounds such as hexahydro-1,3,5tris(2-ethyl)-s-triazine or hexahydro-1,3,5-tris(2-hydroxyethyl)-s-triazine; N-(fluorodichloromethylthio)phthalimide; 3,5-dimethyl-1,3,5-2H-tetrahydrothiadiazine-2-thione; and dithio-2,2'-bis(benzmethylamide). Among those, methylenebisthiocyanate; 5-chloro-2-methyl-4-isothiazolin-3-one, 2-methyl-4-iso-thiazolin-3-one and 4,5-dichloro-2-n-octyl-isothiazolin-3-one and complexes thereof with magnesium chloride or calcium chloride are preferable.

Examples of the organohalogen compounds are organic bromonitro compounds such as 2-bromo-2-nitropropane-1,3diol, 1,1-dibromo-1-nitro-2-propanol, 2,2-dibromo-2-nitro-1-ethanol, 2-bromo-2-nitro-1-ethanol, 1,1-dibromo-1-nitro-2-acetoxyethane, 1,1-dibromo-1-nitro-2acetoxypropane, 2-bromo-2-nitro-1,3-diacetoxypropane, tribromonitromethane, β-bromo-β-nitrostyrene, 5-bromo-5-nitro-1,3-dioxane, 5-bromo-2-methyl-5-nitro-1,3-dioxane, 2-(2-bromo-2-nitroethenyl)furan; organic bromocyano compounds such as 2,2-dibromo-3-nitrilopropionamide, 2-bromo-2-bromo-methyl-glutalonitrile; organic bromocarbonic esters and amides such as 1,2-bis(bromoacetoxy)ethane, 1,2-bis(-bromoacetoxy)propane, 1,4-bis(bromoacetoxy)-2-butene, 1,2,3tris(bromoacetoxy)propane, methylenebis(bromoacetate), benzyl bromoacetate, N-bromoacetoamide, 2-bromoacetoamide, 2-hydroxyethyl-2,3-dibromopropionate. Among those, 2-bromo-2-nitropropan-1,3-diol, 2-bromo-2-nitro-1-ethanol, 2,2-dibromo-2-nitro-1-ethanol, 2-bromo-2-nitro-1,3-diacetoxypropane, 2,2-dibromo-3-nitrilopropionamide, β-bromo-β-nitrostyrene, 5-bromo-5-nitro-1,3-dioxane, 1,2-bis(bromoacetoxy)ethane, 1,2-bis(bromoacetoxy)propane, 1,4-bis(bromoacetoxy)-2-butene and 1,2,3-tris(bromoacetoxy)propane are preferable.

Examples of the organonitrogen compounds include α-chlorobenzaldoxime, α-chlorobenzaldoxime acetate; N,4-(dihydroxy)-α-oxobenzeethaneimidoyl chloride; chlorinated isocyanuric acid compounds such as sodium dichloroisocyanurate and trichloroisocyanuric acid; quarternary ammonium compounds such as dequalinium chloride, alkylisoquinolinium bromide and benzalconium chloride; carbamic acids or esters thereof such as methyl 2-benzimidazolecarbamate and 3-iodo-2-propargylbutylcarbamate or its ester; imidazoles such as 1-[2-(2,4-dichlorophenyl)]-2'-[(2,4dichlorophenyl)methoxy]-ethyl-3-(2-phenylethyl)-1H-imidazolium chloride and 1-[2-(2,4-dichlorophenyl)-2-(2propenyloxy)ethyl]-1H-imidazole; amides such as 2-(2-furyl)-3-(5-nitro-2-furyl)-acrylamide and 2-chloroacetamide; aminoalcohols such as N-(2-hydroxypropyl)-aminomethanol and 2-(hydroxymethylamino) ethanol; sodium 2-pyridinethiol 1-oxide; 5-chloro-2,4,6-trifluoroisophthalonitrile, 5-chloro-2,4-difluoro-6-methoxyisophthalonitrile, 2,4,5,6-tetrachloroisophthalonitrile; 1-bromo-3-chloro-5,5-dimethylhydantoin; N-(2-methyl-1-naphthyl)maleimide and poly[oxyethylene(dimethylimino) ethylene(dimethylimino)ethylenedichloride]. Among those, α-chlorobenzaldoxime; N,4-dihydroxy-α-oxobenzeethaneimidoyl chloride; 5-chloro-2,4,6-trifluoroisophthalonitrile, 5-chloro-2,4-difluoro-6-methoxyisophthalo-nitrile are particularly preferable.

Examples of the organosulfur compounds include 3,3,4,4-tetrachlorotetrahydrothiophene-1,1-dioxide; 4,5-dichloro-1,2-dithiol-3-one; dithio-2,2'-bis(1-benzmethylamide); bis(trichloromethyl)sulfone; bis(tribromomethyl)sulfone; and 2-hydroxypropyl methanethiosulfonate. Among those, 3,3,4,4-tetrachlorotetrahydrothiophene-1,1-dioxide, 4,5-dichloro-1,2-dithiol-3-one, bis(trichloromethyl)sulfone, and bis(tribromomethyl)sulfone are preferable.

The other known microbicidal ingredients include 3-acetoxy-1,1,2-triiodo-1-propene; glutaric dialdehyde; dichlorophene; hydrogen peroxide; and maleic anhydride.

The microbicide for industrial use of the present invention can be used in combination. The preferable combinations are:

i) Monohaloglyoxime and dihaloglyoxime
ii) Monohaloglyoxime and a known industrial microbicidal ingredient
iii) Dihaloglyoxime and a known industrial microbicidal ingredient
iv) Dihaloglyoxime diacylate and a known industrial microbicidal ingredient
v) Monohaloglyoxime, dihaloglyoxime and a known industrial microbicidal ingredient The suitable mixing ratio of the monohaloglyoxime to the dihaloglyoxime are 1:20 to 20:1 and, preferably, 1:10 to 10:1 more preferably 1:3 to 1:1 by weight. In case of simultaneous use of monohaloglyoxime and dihaloglyoxime, the separate preparation containing each of the ingredients can be used if they are synthesized in different processes and the single pack preparation can be used if they are synthesized as a mixture. The suitable mixing ratio of the haloglyoxime derivative (I) to the known industrial microbicidal ingredient is from 20:1 to 1:20 and, preferably, from 10:1 to 1:10.

Further, when three ingredients, i.e., the monohaloglyoxime, the dihaloglyoxime and the known industrial microbicide are combined, the suitable mixing ratio of the monohaloglyoxime and dihaloglyoxime to the known industrial microbicide is from 1:50 to 20:1, preferably from 1:10 to 10:1.

When the above microbicidal ingredients are combined, it is preferable to formulate in the form of liquid preparation, particularly in an aqueous preparation. However, the present invention is not limited thereto. Depending upon the subject to be applied, other forms such as powder may be used.

When the formulation is to be used in an industrial water system, such as in paper making process water or industrial cooling water, the preparation preferably may be prepared by a known method with use of liquid carriers such as water or hydrophilic organic solvents and optionally a surfactant is added.

Examples of the hydrophilic organic solvents are amides, such as N,N-dimethylformamide; glycols such as ethylene glycol, propylene glycol, diethylene glycol and dipropylene glycol; glycol ethers such as methyl cellosolve, phenyl cellosolve, diethylene glycol monomethyl ether, dipropylene glycol monomethyl ether and tripropylene glycol monomethyl ether; alcohols having up to 8 carbon atoms; esters such as methyl acetate, ethyl acetate, 3-metoxybutyl acetate, 2-ethoxymethyl acetate, 2-ethoxyethyl acetate and propylenecarbonate. The above hydrophilic organic solvent can be used in combination with water.

The suitable surfactants include cationic, anionic, nonionic or bifunctional surfactants. Preferable surfactant is nonionic surfactant because of its stability for the preparation.

Examples of the nonionic surfactants include higher alcohol ethylene oxide adducts (hereinafter ethylene oxide is referred to E.O.), alkylphenol-E.O. adducts, fatty acid-E.O. adducts, fatty acid polyhydric alcohol ester-E.O. adducts, higher alkyl amine-E.O. adducts, fatty acid amide-E.O. adducts, fat and oil-E.O. adducts, propylene oxide (hereinafter referred to P.O.)-E.O. copolymers, alkylamine-P.O.-E.O. copolymer adducts, fatty acid glycerol esters, fatty acid pentaerythritol esters, fatty acid sorbitan esters, fatty acid sucrose esters, polyhydric alcohol alkyl ethers and alkylolamides.

The preparation of the present invention preferably comprises 1 to 50 parts by weight of the total preparation of the active ingredients, preferably from 5 to 30 parts by weight, at least 0.01 parts by weight of the surfactant per active ingredient and the balance being the hydrophilic organic solvent.

For an oil medium such as heavy oil sludge, cutting oil or oily paint, a single-pack liquid preparation is formulated with a hydrocarbon solvent such as kerosene, heavy oil and spindle oil, and optionally containing the above-mentioned surfactant.

To the medium in which the active ingredients of the present invention can be directly dissolved or dispersed, the active ingredients may be added directly or in the form of powdery preparation which is diluted with a solid diluent or carrier (e.g. kaolin, clay, bentonite, CMC, etc.) and optionally contains the surfactants. The preparation may be prepared by blending the active ingredients and solid diluents or carriers without solvents and surfactants depending on the combination of the active ingredients.

The suitable use amount of the microbicide of the present invention depends on the industrial medium to be added. In particular, to papermaking process water or industrial cooling water, the addition of about 0.05 to 20 mg/l as the total active ingredients concentration in the water will be sufficient for inhibiting the growth of microbes (bacteriostatic concentration) and the addition of 0.1 to 50 mg/l will achieve a microbicidal effect.

In case of simultaneous use of the above active ingredients, the above mentioned single-pack preparation is convenient to the method according to the present invention. However, if separate storage or separate addition is preferable upon circumstances, for example in case of keeping the stability for a long time, the separate preparations containing each of the active ingredients may be used.

Thus, the present invention provides a method of killing microbes for industrial use by adding the above active ingredients simultaneously or separately to an industrial medium.

Generally, when the active ingredients are added separately, it is convenient to formulate in the form of liquid preparation. The preparation may be formulated by adding the above-mentioned organic solvent or surfactant.

In the above method, the amount (concentration) of the active ingredients to be added and the mixing ratio of the haloglyoxime derivatives to the known industrial microbicidal ingredients depend on the type and the quantity of the microorganisms to be treated and on the type of the industrial microbicidal ingredients. They may be defined by taking the amount and mixing ratio described above into consideration.

EXAMPLES

Now, the present invention is described in detail with reference to synthetic examples, formulation examples, test examples and comparative examples as follows.

Synthetic Example 1: Synthesis of glyoxime

Hydroxylamine sulfate (32.8 g) was dissolved in 70ml of water to which 29.0 g of 40% glyoxal solution were dropwise added. Next, 40% sodium hydroxide solution was added thereto to neutralize. After 30 minutes, the precipitated white crystals were recrystallized from water to give 10.6 g of the title compound (m.p. 178° C.).

Synthesis Example 2: Synthsis of chloroglyoxime and dichloroglyoxime

Glyoxime (8.8 g) obtained in synthetic example 1 was dissolved in 100 ml of methanol. Then, chlorine gas was gradually blown thereto maintaining the temperature at 10° to 12° C.

Upon examination of the resulting product by HPLC, it shows that chloroglyoxime is produced (reaction A), followed by the formation of dichloroglyoxime (reaction B).

$$HO-N=C-C=N-OH \atop H \quad H \xrightarrow{Cl_2} \text{(reaction A)}$$

$$HO-N=C-C=N-OH \atop H \quad Cl \xrightarrow{Cl_2} \text{(reaction B)}$$

$$HO-N=C-C=N-OH \atop Cl \quad Cl$$

The reaction was ceased at the reaction A stage and the solvent was removed. The residue was recrystallized from water, affording white crystals of chloroglyoxime (m.p. 156° C., yield: 36%).

Also, the reaction was stopped at the reaction B stage. The solvent was removed and the residue was recrystallized from ethanol, affording white crystals of dichloroglyoxime (m.p. 199° C., yield: 55%).

Synthetic Example 3: Synthesis of dichloroglyoxime diacetate

The mixture of 2.0 g (0.0127 mol) of dichloroglyoxime (Compound No.6), 20 ml of dichloroethane and 2.4 g (0.0306 mol) of acetyl chloride was stirred in an ice bath. To the mixture, triethylamine (3.1 g, 0.0307 mol) was added dropwise, followed by stirring for 30 minutes. The reaction mixture was washed twice with 15 ml of water. The dichloroethane solution was concentrated under reduced pressure, to obtain white crystals of dichloroglyoxime diacetate (Compound No.2, yield: 30%).

Compounds Nos.3 to 5 were prepared in the same way, except for using the corresponding acid chloride.

Table 1 shows structural formulae and physical properties of the products.

TABLE 1

| Comp. No. | Structural Formula | MP. °C. | IR (ester) cm$^{-1}$ | $^1$H-NMR ppm | $^{13}$C-NMR ppm |
|---|---|---|---|---|---|
| 1 | CH$_3$—C(=O)—O—N=C(Cl)—C(Cl)=N—O—C(=O)—CH$_3$ | 156 | 1820 | 2.33 | 18.9, 139.7, 165.7 |
| 2 | CH$_3$CH$_2$—C(=O)—O—N=C(Cl)—C(Cl)=N—O—C(=O)—CH$_2$CH$_3$ | 66 | 1800 | 1.23, 2.61 | 8.7, 25.8, 139.8, 169.4 |
| 3 | CH$_3$CH$_2$CH$_2$—C(=O)—O—N=C(Cl)—C(Cl)=N—O—C(=O)—CH$_2$CH$_2$CH$_3$ | 70 | 1790 | 1.04, 1.76, 2.56 | 13.4, 18.0, 34.0, 139.7, 168.4 |
| 4 | (CH$_3$)$_2$CH—C(=O)—O—N=C(Cl)—C(Cl)=N—O—C(=O)—CH(CH$_3$)$_2$ | 64 | 1795 | 1.32, 2.85 | 18.6, 32.6, 140.0, 171.5 |
| 5 | ClCH$_2$—C(=O)—O—N=C(Cl)—C(Cl)=N—O—C(=O)—CH$_2$Cl | 140 | 1800 | 4.37 | 39.0, 141.6, 169.7 |
| 6 | HO—N=C(Cl)—C(Cl)=N—OH, Dichloroglyoxime | 196 | — | — | 131.1, 131.2 |

| | Parts by weight |
|---|---|
| Formulation Example 1 | |
| Monochloroglyoxime | 5 |
| Water | 95 |
| Formulation Example 2 | |
| Monochloroglyoxime | 20 |
| Diethylene glycol | 60 |
| Water | 20 |
| Formulation Example 3 | |
| Monochloroglyoxime | 5 |
| Diethylene glycol monomethyl ether | 85 |
| Water | 10 |
| Formulation Example 4 | |
| Monochloroglyoxime | 5 |
| Dichloroglyoxime | 5 |
| Diethyleneglycol | 79 |
| Water | 10 |
| Polyoxyethylene nonylphenylether (EO10) | 1 |
| Formulation Example 5 | |
| Dichloroglyoxime diacetate | 10 |
| Dimethyl glutarate | 90 |
| Formulation Example 6 | |
| Dichloroglyoxime dipropionate | 10 |
| Dimethyl glutarate | 90 |
| Formulation Example 7 | |
| Dichloroglyoxime dinormalbutyrate | 10 |
| Dimethyl glutarate | 90 |
| Formulation Example 8 | |
| Dichloroglyoxime diisobutyrate | 5 |
| Dimethyl glutarate | 95 |
| Formulation Example 9 | |
| Bis(chloroacetyl)dichloroglyoxime | 10 |
| Dimethyl glutarate | 90 |

The abbreviations of test compounds are listed below.

TABLE 2

| Abbreviation | Compound |
|---|---|
| MCG | Monochloroglyoxime |
| DCG | Dichloroglyoxime |
| DCGE | Dichloroglyoxime dipropionate |
| C | Methylenebis(thiocyanate) |
| D | 9:1 mixture of 5-chloro-2-methyl-4-isothiazolin-3-one and 2-methyl-4-isothiazolin-3-one |
| E | α-chlorobenzaldoxime |
| F | Bis(tribromomethyl)sulfone |
| G | 2,2-dibromo-3-nitrilopropionamide |
| H | 2-bromo-2-nitro-1,3-propanediol |
| I | 2,2-dibromo-2-nitro-1-ethanol |
| J | 2-bromo-2-nitro-1-ethanol |
| K | 2-bromo-2-nitro-1,3-diacetoxy-propane |
| L | 1,2-bis(bromoacetoxy)ethane |
| M | 1,2-bis(bromoacetoxy)propane |
| N | 1,4-bis(bromoacetoxy)-2-butene |
| O | 1,2,3-tris(bromoacetoxy)propane |
| P | 5-chloro-2,4,6-trifluoroisophthalonitrile |
| Q | 5-chloro-2,4-difluoro-6-methoxyisophthalonitrile |
| R | 3,3,4,4-tetrachlorotetrahydro-thiophene-1,1-dioxide |
| S | β-bromo-β-nitrostyrene |
| T | 5-bromo-5-nitro-1,3-dioxane |
| U | Bis(trichloromethyl)sulfone |
| V | 4,5-dichloro-2-n-octyl-isothiazolin-3-one |
| W | 4,5-dichloro-1,2-dithiol-3-one |

Tables 3 to 12 show other formulation examples.

TABLE 3

| Compound | \multicolumn{8}{c|}{Formulation No.} |
|---|---|---|---|---|---|---|---|---|
|  | 10 | 11 | 12 | 13 | 14 | 15 | 16 | 17 |
| Prescription |  |  |  |  |  |  |  |  |
| MCG | 10 | 10 | 10 | 10 | 10 | 10 | 10 | 10 |
| C | 10 |  |  |  |  |  |  |  |
| D |  |  | 5 |  |  |  |  |  |
| E |  |  |  | 10 |  |  |  |  |
| F |  |  |  |  | 10 |  |  |  |
| G |  |  |  |  |  | 10 |  |  |
| H |  |  |  |  |  |  | 10 |  |
| I |  |  |  |  |  |  |  | 10 |
| K |  |  |  |  |  |  |  | 10 |
| Ethyleneglycol |  | 45 |  |  | 30 |  |  |  |
| Diethyleneglycol | 29 |  |  | 79 | 70 |  | 79 |  |
| Diethyleneglycol monomethyl ether | 50 | 30 | 79 |  |  |  |  |  |
| Water |  | 10 |  |  | 10 | 50 |  |  |
| Nonylphenol EO (10 mol) adduct | 1 |  | 1 | 1 |  |  | 1 |  |
| Propylene carbonate |  |  |  |  |  |  |  | 80 |

TABLE 4

| Compound | \multicolumn{8}{c|}{Formulation No.} |
|---|---|---|---|---|---|---|---|---|
|  | 18 | 19 | 20 | 21 | 22 | 23 | 24 | 25 |
| Prescription |  |  |  |  |  |  |  |  |
| MCG | 10 | 10 | 10 | 10 | 5 | 10 | 5 | 10 |
| L | 10 |  |  |  |  |  |  |  |
| M |  | 10 |  |  |  |  |  |  |
| N |  |  | 10 |  |  |  |  |  |
| O |  |  |  | 10 |  |  |  |  |
| P |  |  |  |  | 5 | 1 |  |  |
| Q |  |  |  |  |  |  | 5 | 1 |
| Ethyleneglycol |  |  |  |  |  |  |  |  |
| Diethyleneglycol | 20 |  |  |  |  |  |  |  |
| Diethyleneglycol methyl ether |  | 20 | 20 | 20 |  |  |  |  |
| Water |  |  |  |  |  |  |  |  |
| Nonylphenol EO (10 mol) adduct | 1 | 1 | 1 | 1 | 1 | 1 | 1 | 1 |
| Propylene carbonate | 59 | 59 | 59 | 59 | 89 |  |  | 88 |
| Dimethyl glutarate |  |  |  |  |  | 88 | 89 |  |

TABLE 5

| Compound | \multicolumn{9}{c|}{Formulation No.} |
|---|---|---|---|---|---|---|---|---|---|
|  | 26 | 27 | 28 | 29 | 30 | 31 | 32 | 33 | 34 |
| Prescription |  |  |  |  |  |  |  |  |  |
| MCG | 9 | 1 | 8 | 2 | 5 | 9.5 | 5 | 0.5 | 9 |
| DCG | 1 | 9 | 2 | 8 | 5 | 0.5 | 5 | 9.5 | 1 |
| C | 10 | 10 |  |  |  |  |  |  |  |
| D |  |  | 5 | 5 |  |  |  |  |  |
| E |  |  |  |  | 10 | 10 |  |  |  |
| F |  |  |  |  |  |  | 10 | 10 |  |
| G |  |  |  |  |  |  |  |  | 10 |
| Ethyleneglycol |  |  | 45 | 45 |  |  |  |  |  |
| Diethyleneglycol | 29 | 29 |  |  |  |  | 79 | 79 | 70 |
| Diethyleneglycol monomethyl ether | 50 | 50 | 29.9 | 30 | 79 | 79 |  |  |  |
| Water |  |  | 10 | 10 |  |  |  |  | 10 |
| Nonylphenol EO (10 mol) adduct | 1 | 1 | 0.1 |  | 1 | 1 | 1 | 1 |  |
| Propylene-carbonate |  |  |  |  |  |  |  |  |  |

TABLE 6

| Compound | \multicolumn{9}{c|}{Formulation No.} |
|---|---|---|---|---|---|---|---|---|---|
|  | 35 | 36 | 37 | 38 | 39 | 40 | 41 | 42 | 43 |
| Prescription |  |  |  |  |  |  |  |  |  |
| MCG | 1 | 7 | 3 | 5 | 8 | 9 | 1 | 9 | 1 |
| DCG | 9 | 3 | 7 | 5 | 2 | 1 | 9 | 1 | 9 |
| G | 10 |  |  |  |  |  |  |  |  |
| H |  | 10 | 10 |  |  |  |  |  |  |
| I |  |  |  | 10 | 10 |  |  |  |  |
| K |  |  |  |  |  | 10 | 10 |  |  |
| L |  |  |  |  |  |  |  | 10 | 10 |
| Ethyleneglycol |  |  | 30 |  |  |  |  |  |  |
| Diethyleneglycol | 70 | 70 |  | 79 | 79 |  |  | 20 | 20 |
| Diethyleneglycol monomethyl ether |  |  | 50 |  |  |  |  |  |  |
| Water | 10 | 10 |  |  |  |  |  | 1 | 1 |
| Nonylphenol EO (10 mol) adduct |  |  |  | 1 | 1 |  |  | 1 | 1 |
| Propylene carbonate |  |  |  |  |  | 80 | 80 | 59 | 59 |

TABLE 7

| Compound | \multicolumn{8}{c|}{Formulation No.} |
|---|---|---|---|---|---|---|---|---|
|  | 44 | 45 | 46 | 47 | 48 | 49 | 50 | 51 |
| Prescription |  |  |  |  |  |  |  |  |
| MCG | 5 | 8 | 5 | 2 | 9 | 1 | 5 | 5 |
| DCG | 5 | 2 | 5 | 8 | 1 | 9 | 5 | 5 |
| M | 10 | 10 |  |  |  |  |  |  |
| N |  |  | 10 | 10 |  |  |  |  |
| O |  |  |  |  | 10 | 10 |  |  |
| P |  |  |  |  |  |  | 5 |  |
| Q |  |  |  |  |  |  |  | 5 |
| Diethyleneglycol monomethyl ether | 20 | 20 | 20 | 20 | 20 | 20 |  |  |
| Water |  |  |  |  |  |  |  |  |
| Nonylphenol EO (10 mol) adduct | 1 | 1 | 1 | 1 | 1 | 1 | 1 | 1 |
| Propylene carbonate | 59 | 59 | 59 | 59 | 59 | 59 |  | 84 |
| Dimethyl glutarate |  |  |  |  |  |  | 84 |  |

TABLE 8

| Compound | \multicolumn{10}{c}{Formulation No.} | | | | | | | | | |
|---|---|---|---|---|---|---|---|---|---|---|
| | 52 | 53 | 54 | 55 | 56 | 57 | 58 | 59 | 60 | 61 |
| Prescription | | | | | | | | | | |
| MCG | 5 | 5 | 5 | 5 | 5 | 0.5 | 0.5 | 4.5 | 4.5 | 4.5 |
| DCG | | | | | | 4.5 | 4.5 | 0.5 | 0.5 | 4.5 |
| R | 5 | | | | 5 | | | | | |
| S | | 5 | | | | | 5 | | | |
| T | | | 5 | | | | | 5 | | |
| U | | | | 5 | | | | | 5 | |
| V | | | | | 5 | | | | | 5 |
| N,N-dimethylformamide | 10 | 10 | | 10 | 10 | 10 | 10 | | 10 | 10 |
| Diethyleneglycol | | | 80 | | | | | 80 | | |
| Diethyleneglycol monomethyl ether | 79 | 79 | | 79 | 79 | 79 | 79 | | 79 | 79 |
| Water | | | 10 | | | | | 10 | | |
| Nonylphenol EO (10 mol) adduct | 1 | 1 | | 1 | 1 | 1 | 1 | | 1 | 1 |

TABLE 9

| Compound | \multicolumn{6}{c}{Formulation No.} | | | | | |
|---|---|---|---|---|---|---|
| | 62 | 63 | 64 | 65 | 66 | 67 |
| Prescription | | | | | | |
| MCG | | | 1 | | 5 | 1 | 9 |
| DCG | 5 | | 10 | 5 | 9 | 1 |
| W | 5 | 10 | 1 | 5 | 5 | 5 |
| Diethyleneglycol monomethyl ether | 29 | 58 | | 24 | 24 | 24 |
| Diethyleneglycol | 60 | 30 | 88 | 60 | 60 | 60 |
| Nonylphenol EO (10 mol) adduct | 1 | 1 | 1 | 1 | 1 | 1 |

TABLE 10

| Compound | \multicolumn{10}{c}{Formulation No.} | | | | | | | | | |
|---|---|---|---|---|---|---|---|---|---|---|
| | 68 | 69 | 70 | 71 | 72 | 73 | 74 | 75 | 76 | 77 |
| Prescription | | | | | | | | | | |
| DCG | 10 | 10 | 10 | 10 | 10 | 10 | 10 | 10 | 10 | 10 |
| C | 10 | | | | | | | | | |
| D | | 5 | | | | | | | | |
| E | | | 10 | | | | | | | |
| F | | | | 10 | | | | | | |
| G | | | | | 10 | | | | | |
| H | | | | | | 10 | | | | |
| I | | | | | | | 10 | | | |
| J | | | | | | | | 10 | | |
| K | | | | | | | | | 10 | |
| L | | | | | | | | | | 10 |
| Ethyleneglycol | | 45 | | | | | | | | |
| Diethyleneglycol | 29 | | | | 79 | 70 | 70 | 79 | 80 | 20 |
| Diethyleneglycol methyl ether | 50 | 29.9 | 79 | | | | | | | |
| Water | | 10 | | | 10 | 10 | | | | |
| Nonylphenol EO (10 mol) adduct | 1 | 0.1 | 1 | 1 | | | 1 | | | 1 |
| Propylene carbonate | | | | | | | | | 80 | 59 |

TABLE 11

| Compound | \multicolumn{13}{c}{Formulation No.} | | | | | | | | | | | | |
|---|---|---|---|---|---|---|---|---|---|---|---|---|---|
| | 78 | 79 | 80 | 81 | 82 | 83 | 84 | 85 | 86 | 87 | 88 | 89 | 90 |
| Prescription | | | | | | | | | | | | | |
| DCG | 10 | 10 | 10 | 5 | 1 | 5 | 1 | 5 | 5 | 5 | 5 | 5 | 5 |
| X | 10 | | | | | | | | | | | | |
| N | | 10 | | | | | | | | | | | |
| O | | | 10 | | | | | | | | | | |
| P | | | | 5 | 10 | | | | | | | | |
| Q | | | | | | 5 | 10 | | | | | | |
| R | | | | | | | | 5 | | | | | |
| S | | | | | | | | | 5 | | | | |
| T | | | | | | | | | | 5 | | | |
| U | | | | | | | | | | | 5 | | |
| V | | | | | | | | | | | | | |
| W | | | | | | | | | | | | | |
| Ethyleneglycol | | | | | | | | | | | 80 | | |
| Diethyleneglycol | | | | | | | | 79 | 79 | | | 79 | 79 |
| Diethyleneglycol methyl ether | 20 | 20 | 20 | | | | | | | | | | 29 |
| Water | | | | | | | | | | 10 | | | |
| Nonylphenol EO (10 mol) adduct | 1 | 1 | 1 | 1 | 1 | 1 | 1 | 1 | 1 | | | 1 | 1 |
| Propylene carbonate | 59 | 59 | 59 | | 88 | 89 | | | | | | | |
| Dimethyl glutarate | | | | 89 | | | 88 | | | | | | |
| N,N-dimethylformamide | | | | | | | | 10 | 10 | | | 10 | 10 |

TABLE 12

| Compound | \multicolumn{12}{c}{Formulation No.} | | | | | | | | | | | |
|---|---|---|---|---|---|---|---|---|---|---|---|---|
| | 91 | 92 | 93 | 94 | 95 | 96 | 97 | 98 | 99 | 100 | 101 | 102 |
| Prescription | | | | | | | | | | | | |
| DCGE | | | 10 | 10 | 10 | 10 | 10 | 10 | 10 | 10 | 10 | 10 |
| D | 5 | | | | | | | | | | | |
| E | | 5 | | | | | | | | | | |
| G | | | 10 | | | | | | | | | |
| H | | | | 10 | | | | | | | | |
| I | | | | | 10 | | | | | | | |
| K | | | | | | 10 | | | | | | |

TABLE 12-continued

| Compound | Formulation No. | | | | | | | | | | | |
|---|---|---|---|---|---|---|---|---|---|---|---|---|
| | 91 | 92 | 93 | 94 | 95 | 96 | 97 | 98 | 99 | 100 | 101 | 102 |
| N | | | | | | | 10 | | | | | |
| P | | | | | | | | 10 | | | | |
| R | | | | | | | | | 10 | 10 | | |
| S | | | | | | | | | | | 5 | |
| W | | | | | | | | | | | | 5 |
| Ethyleneglycol | | 45 | | | | | | | | | | |
| Diethyleneglycol | | | | 20 | | | | | 20 | | | |
| Diethyleneglycol methyl ether | 20 | 20 | | | | | | | | | 20 | 20 |
| Water | | | | | | | | | | | | |
| Nonylphenol EO (10 mot) adduct | 1 | 1 | 1 | | | | | | | | | |
| Propylene carbonate | 64 | 39 | | 79 | 80 | | 80 | | 80 | | 65 | 65 |
| Dimethyl glutarate | | | 60 | | | 80 | | 80 | | 60 | | |

Test Example 1: (Evaluation of Microbicidal Effect on Standard Strains)

Microbicidal effect on standard strains of various bacteria was tested.

To a phosphate buffer having pH7.0, a bacteria containing solution preincubated in bouillon medium was added so as to have a viable cell number of $10^6$ cfu/ml. Then, to the mixture, monochloroglyoxime or 1-chloro-2-methylglyoxime was added and shaken for 60 minutes at 30° C. The number of surviving cells was counted and the minimum concentration for killing the bacteria 99.9% or more was calculated.

The result is shown in table 13.

TABLE 13

| | Minimum microbicidal concentration (mg/l) | |
|---|---|---|
| Standard microorganism | monochloro-glyoxime | 1-chloro-2-methyl-glyoxime |
| Pseudomonas aeruginosa | 0.2 | 0.3 |
| Escherichia coli | 0.2 | 0.1 |
| Alcaligenes faecalis | 0.3 | 0.2 |
| Micrococcus luteus | 0.4 | 0.5 |
| Bacillus subtilis | 0.3 | 0.3 |

Test Example 2: (Evaluation of Microbicidal Effect in the Presence of a Reducing Substance)

Flavobacterium sp. isolated from pink slime generated in a certain paper mill was used to evaluate the microbicidal effect in the presence of a reducing substance of sodium sulfite. To a pH7.0 buffer containing 0, 10 or 50 mg/l of $SO_3^{2-}$, a bacteria containing water preincubated in bouillon medium was added so as to have a viable cell number of $10^6$ cfu/ml. Then, microbicidal ingredient was added thereto and shaken for 60 minutes at 30° C. The number of surviving cells was counted and the minimum concentration for killing the bacteria 99.9% or more was calculated.

The result are shown in table 14 with comparative examples.

TABLE 14

| | | Minimum Microbicidal Concentration (mg/l) | | |
|---|---|---|---|---|
| | Structural formula of ingredient | $SO_3^{2-}$ concentration (mg/l) | | |
| | | 0 | 10 | 50 |
| (Example) | HO—N=C—C=N—OH <br> \| \| <br> Cl H (MCG) | 0.1 | 0.5 | 2.5 |
| (Comparative) | HO—N=C—C=N—OH <br> \| \| <br> Cl Cl (DCG) | 1.0 | 5 | 30 |
| (Comparative) | HO—N=C—C=N—OH <br> \| \| <br> H H | >100 | >100 | >100 |

Test Example 3: (Evaluation of Microbicidal Effect on Bacteria)

Pseudomonas aeruginosa as a gram-negative bacteria and Staphylococcus aureus as a gram-positive bacteria were used to determine a minimum concentration of bacteriocidal ingredient capable of killing bacteria 99.9% or more, i.e., to reduce the number of viable cell from $10^6$ cfu/ml to $10^3$ cfu/ml or below.

First, a bacteria solution preincubated by bouillon medium was added to saline so as to have a viable cell number of $10^6$ cfu/ml or more. Then, microbicidal ingredient was added thereto and shaken for 60 minutes at 37° C. The number of surviving cells was counted and the minimum concentration for killing the bacteria 99.9% or more was calculated.

The result is shown in Table 15.

TABLE 15

| Minimum Microbicidal Concentration (mg/l) | | |
|---|---|---|
| Compound No.* | P. aeruginosa | S. aureus |
| 1 | 0.3 | 0.4 |
| 2 | 0.2 | 0.3 |
| 3 | 0.4 | 0.4 |
| 4 | 0.4 | 0.4 |
| 5 | 0.5 | 0.3 |
| 6 (Comparative) | 1.1 | 1.5 |

*See Table 1 for Compound Nos. 1 to 6.

Testing Example 4: (Evaluation of Fungicidal Effect on Yeast)

*Candida albicans* was used to determine a minimum concentration of fungicidal ingredient capable of killing it 99.9% or more, i.e., to reduce the number of viable cells from $10^5$ cfu/ml to $10^2$ cfu/ml or below.

First, a yeast solution preincubated by YM medium was added to saline so as to have a viable cell number of $10^5$ cfu/ml or more. Then, fungicidal ingredient was added thereto and shaken for 60 minutes at 37° C. The number of surviving cells was counted and the minimum concentration for killing the yeast 99.9% or more was calculated.

The result is shown in Table 16.

TABLE 16

| Minimum Fungicidal Concentration (mg/l) | |
| --- | --- |
| Compound No.* | *C. albicans* |
| 1 | 0.5 |
| 2 | 0.4 |
| 3 | 0.6 |
| 4 | 0.5 |
| 5 | 0.5 |
| 6 (Comparative) | 1.9 |

*See Table 1 for Compound Nos. 1 to 6.

Test Example 5: (Evaluation of Microbicidal Effect on Fungi)

*Aspergillus niger* was used to determine a minimum inhibitory concentration of microbicidal ingredient to inhibit the growth thereof.

First, 1 loop of spore was sampled from stored *Aspergillus niger* which was previously slant-cultured. The spore was suspended in 10 ml of aseptic water. Then, a certain amount of the suspended solution and predetermined amount of microbicidal ingredient were inoculated in Czapek's medium and shaken for 7 days at 27° C. The minimum concentration of ingredient was determined at which no growth of hypha was identified.

The result is shown in Table 17.

TABLE 17

| Minimum Growth Inhibitory Concentration (mg/l) | |
| --- | --- |
| Compound Nos.* | *A. niger* |
| 1 | 0.4 |
| 2 | 0.4 |
| 3 | 0.9 |
| 4 | 0.8 |
| 5 | 0.5 |
| 6 (Comparative) | 1.7 |

Test Example 6: (Evaluation of Microbicidal Effect on white water sampled from the process for making high quality neutral paper)

In a certain paper mill, white water (pH of 7.5, containing Pseudomonas, Bacillus, Staphylococcus, Micrococcus and Flavobacterium species) was sampled from a high quality papermaking machine. Microbicidal ingredients were added thereto and shaken for 60 minutes at 37° C. Then, the number of surviving cells was counted and the minimum concentration of the microbicidal ingredient for killing bacteria 99.9% or more of the initial bacteria (8.1 x $10^6$ cfu/ml) was determined.

The result is shown in Table 18.

TABLE 18

| Minimum Microbicidal Concentration (mg/l) | |
| --- | --- |
| Compound No. | High quality neutralized water |
| 1 | 1.0 |
| 2 | 0.8 |
| 3 | 1.0 |
| 4 | 1.1 |
| 5 | 1.0 |
| 6 (Comparative) | 2.2 |

Test Example 7: (Evaluation of Microbicidal Effect on white water sampled from process for making an acidic newsprint paper)

In a certain paper mill, white water (pH4.6, $SO_3^{2-}$: 11 mg/l containing Pseudomonas, Staphylococcus, Alcaligenes, Flavobacterium and Bacillus species) was sampled from a newsprint papermaking machine. Microbicidal ingredient was added thereto and shaken for 60 minutes at 37° C. Then, the number of surviving cells was counted and the minimum concentration of the microbicidal ingredient for killing 99.9% or more of the initial bacteria ($2.5 \times 10^6$ cfu/ml) was determined.

The result is shown in Table 19.

TABLE 19

| Minimum Microbicidal Concentration (mg/l) | |
| --- | --- |
| Compound No. | Acidic Newsprint Paper |
| 1 | 1.0 |
| 2 | 0.9 |
| 3 | 1.1 |
| 4 | 1.2 |
| 5 | 0.9 |
| 6 (Comparative) | 3.0 |

Test Example 8: (Evaluation of Synergistic Effect of monochloroglyoxime and dichloroglyoxime)

*Psudomonas aeruginosa* was preincubated in bouillon medium and added to phosphate buffer (pH 7.0) so as to contain the number of viable cells of $10^6$ cfu/ml or more. Then, monochloroglyoxime and dichloroglyoxime were added thereto in the amount of 0.1 mg/l in total in a predetermined ratio and shaken for 60 minutes at 30° C. The number of surviving cells was counted and the killing rate was calculated. The initial number of viable cells was $2.1 \times 10^6$ cfu/ml.

The result is shown in Table 20.

TABLE 20

| MCG:DCG | Added amount (mg/l) | Number of viable cells (cfu/ml) | Killing rate (%) |
| --- | --- | --- | --- |
| Control | | | |
| — | 0 | $2.1 \times 10^6$ | — |
| 1:0 | 0.1 | $4.5 \times 10^5$ | 78.6 |
| 10:1 | 0.1 | $2.5 \times 10^4$ | 98.8 |
| 5:1 | 0.1 | $3 \times 10^3$ | 99.9 |
| Example | | | |
| 3:1 | 0.1 | $1 \times 10^3$ or less | 99.9 or more |
| 1:1 | 0.1 | $1 \times 10^3$ or less | 99.9 or more |
| 1:3 | 0.1 | $1.5 \times 10^4$ | 99.3 |
| 1:5 | 0.1 | $1.8 \times 10^5$ | 85.7 |
| 1:10 | 0.1 | $3.9 \times 10^5$ | 81.4 |
| Comparative | | | |

TABLE 20-continued

| MCG:DCG | Added amount (mg/l) | Number of viable cells (cfu/ml) | Killing rate (%) |
|---|---|---|---|
| 0:1 | 0.1 | $2.1 \times 10^6$ | 0 |

$$\text{Killing rate (\%)} = \frac{\text{Viable cell number (initial)} - \text{Viable cell number (surviving)}}{\text{Viable cell number (initial)}} \times 100$$

Test Example 9: (Evaluation of Microbicidal Effect on white water from various paper mills (No.1))

White waters as listed in Table 21 below were sampled from various paper mills. To the white water, monochloroglyoxime (MCG) alone, the combination of MCG and dichloroglyoxime (DCG) mixed in the ratio of 1:1, and DCG alone are respectively added and shaken for 30 minutes at 30° C. Then, the number of surviving cells was counted.

The result is shown in Table 22.

TABLE 21

| White water type | Paper to be made | pH | $SO_3^{2-}$ (mg/l) | Viable cell number (cfu/ml) | *Species of bacteria |
|---|---|---|---|---|---|
| a | High quality (neutralized) | 7.6 | 0 | $2.7 \times 10^7$ | Ps, Ba, Mi |
| b | Standard (neutralized) | 7.6 | 20 | $1.0 \times 10^7$ | Fl, Al, Mi, Ba |
| c | Newspaper | 4.6 | 15 | $2.0 \times 10^6$ | Ps, Fl, St |
| d | Cardboard | 6.6 | 23 | $5.5 \times 10^7$ | Ps, Fl, Al, Ba |

Species:
Ps: *Pseudomanas sp.*
Fl: *Flavobacterium sp.*
Al: *Alcaligenes sp.*
Ba: *Bacillus sp.*
St: *Staphylococcus sp.*
Mi: *Micrococcus sp.*

TABLE 22

| White water type | Ingredient added (mg/l) | Viable cell number (cfu/ml) | | |
|---|---|---|---|---|
| | | MCG | MCG + DCG (1:1) | DCG |
| a | 0.5 | $4.5 \times 10^4$ | $2.0 \times 10^3$ | $2.0 \times 10^6$ |
| b | 2.5 | $7.8 \times 10^4$ | $9.7 \times 10^3$ | $9.7 \times 10^4$ |
| c | 1.5 | $3.5 \times 10^3$ | $2.1 \times 10^2$ | $2.1 \times 10^5$ |
| d | 1.5 | $4.5 \times 10^5$ | $4.3 \times 10^4$ | $4.3 \times 10^7$ |
| | 10 | $1 \times 10^3$ or less | $1 \times 10^3$ or less | $6.1 \times 10^5$ |
| | | Examples | | Comparative |

Test Example 10: (Evaluation of Bacteriostatic Effect as Slime Controlling Agent in Industrial Water System)

Slimes generated in sprinkle board and wall of hot water pit in open circulating cooling tower system were dispersed in an industrial water and filtered with filter paper (No.2) to prepare test water (pH: 7.2, viable cell number: $2.0 \times 10^6$ cfu/ml, microorganisms: Pseudomonas sp., Flavobacterium sp., Alcaligenes sp. and Bacillus sp.).

Bouillon medium was added to the test water. The mixture was put to a previously sterilized L shaped test tube, to which a definite amount of microbicidal ingredient was added and cultivated under shaking at 30° C. for 24 hours. Then, the turbidity caused by the growth of microorganism was measured by an absorbance at 660 nm whereupon the effect was judged.

The minimum amount whereby no increase in absorbance by addition of the ingredient was noted, i.e., minimum inhibitory concentration (MIC, 24 hr) of the ingredient was determined.

The result is shown in Table 23.

TABLE 23

| Minimum Growth Inhibitory Concentration (mg/l) | | | |
|---|---|---|---|
| Ingredient | MIC 24 Hr (mg/l) | Ingredient | MIC 24 Hr (mg/l) |
| MCG | 0.8 | MCG:DCG:C = 1:1:1 | 0.2 |
| DCG | 0.9 | MCG:DCG:D = 1:1:1 | 0.2 |
| C | 0.8 | MCG:C = 1:1 | 0.3 |
| D | 0.8 | MCG:D = 1:1 | 0.3 |
| H | 1.0 | MCG:H = 1:1 | 0.4 |
| | | MCG:DCG:H = 1:1:1 | 0.2 |

Test Example 11: (Evaluation of Bacteriostatic Effect on White Water from Paper Mill (No.1))

White water sampled from a papermaking mill (I) (paper: high quality paper by acid paper making, pH: 4.3, $SO_3^{2-}$: 0 mg/l, viable cell number: $5.5 \times 10^5$ cfu/ml, microorganism: Bacillus, Pseudomonas, Flavobacterium and Alcaligenes), was filtered through filter paper (No.2) to prepare test water. Bouillon medium was added to the test water. The resultant was put to a previously sterilized L shaped test tube, to which bacteriostatic ingredient was added and cultivated under shaking at 30° C. for 24 hours. Then, the turbidity caused by the growth of microorganism was measured by an absorbance at 660 nm whereupon the bacteriostatic effect was judged.

The minimum amount whereby no increase in absorbance by addition of the ingredient was noted, i.e., minimum inhibitory concentration (MIC, 24 h) of the ingredients was determined.

The result is shown in Table 24.

TABLE 24

| Minimum Growth Inhibitory Concentration (mg/l) | | |
|---|---|---|
| Mill No. | Ingredient | MIC 24 Hr (mg/l) |
| I | MCG | 0.4 |
| | DCG | 0.5 |
| | C | 0.7 |
| | D | 0.5 |
| | G | 2.0 |
| | MCG:DCG:C = 1:9:10 | 0.05 |
| | MCG:DCG:D = 1:9:10 | 0.05 |
| | MCG:C = 1:1 | 0.15 |
| | MCG:D = 1:1 | 0.10 |
| | MCG:G = 1:1 | 0.20 |
| | MCG:DCG:G = 9:1:10 | 0.05 |

Test Example 12: (Evaluation of Bacteriostatic Effect on white water from papermaking mill (No.2))

White water sampled from each of a papermaking mills (II) to (V) was filtered through filter paper (No.2) to prepare test water. Test water is listed in Table 25.

Bouillon medium was added to the test water. The resultant was put to a previously sterilized L shaped test tube, to which microbicidal ingredient was added and cultivated under shaking at 30° C. for 24 hours. Then, the turbidity caused by the growth of bacteria was measured by an absorbance at 660 nm whereupon the effect was judged. The minimum amount whereby no increase in absorbance by addition of the ingredient was noted (minimum inhibitory concentration) (MIC, 24 h) of the ingredient was determined.

The result is shown in Tables 26 to 29.

TABLE 25

| Mill No. | Paper to be made | pH | SO$_3^{2-}$ (mg/l) | Viable cell number (cfu/l) | *Species of microorganism |
|---|---|---|---|---|---|
| II | High quality (neutralized) | 7.6 | 0 | $1.1 \times 10^6$ | Ps, Fl, Al, Ba |
| III | Standard (neutralized) | 7.5 | 15 | $1.0 \times 10^7$ | Ps, Fl, Ba, Mi |
| IV | Newspaper | 4.5 | 10 | $2.1 \times 10^6$ | Ps, Al, St |
| V | Cardboard | 6.0 | 20 | $1.1 \times 10^8$ | Ps, Fl, Al |

TABLE 26

Minimum Growth Inhibitory Concentration (mg/l)

| Mill No. | Ingredient | MIC 24 Hr (mg/l) |
|---|---|---|
| II | MCG | 0.7 |
| | DCG | 1.0 |
| | C | 1.5 |
| | D | 1.0 |
| | MCG:DCG:C = 9:1:10 | 0.15 |
| | MCG:DCG:D = 9:1:10 | 0.15 |
| | MCG:C = 1:1 | 0.3 |
| | MCG:D = 1:1 | 0.3 |
| | MCG:DCG:C = 1:9:10 | 0.10 |
| | MCG:DCG:D = 1:9:10 | 0.10 |

TABLE 27

Minimum Growth Inhibitory Concentration (mg/l)

| Mill No. | Ingredient | MIC 24 Hr (mg/l) |
|---|---|---|
| III | MCG | 3.0 |
| | DCG | 4.0 |
| | G | 5.0 |
| | K | 5.0 |
| | E | 4.5 |
| | MCG:DCG:G = 9:1:10 | 0.3 |
| | MCG:DCG:G = 1:9:10 | 0.3 |
| | MCG:G = 1:1 | 0.8 |
| | MCG:K = 1:1 | 0.8 |
| | MCG:E = 1:1 | 0.7 |
| | MCG:DCG:K = 1:1:2 | 0.5 |
| | MCG:DCG:E = 1:1:2 | 0.5 |

TABLE 28

Minimum Growth Inhibitory Concentration (mg/l)

| Mill No. | Ingredient | MIC 24 Hr (mg/l) |
|---|---|---|
| IV | MCG | 1.5 |
| | DCG | 2.0 |
| | L | 4.0 |
| | M | 4.0 |
| | N | 2.5 |
| | O | 5.0 |
| | MCG:DCG:L = 9:1:10 | 0.3 |
| | MCG:DCG:M = 1:1:2 | 0.3 |
| | MCG:L = 1:1 | 0.5 |
| | MCG:M = 1:1 | 0.5 |
| | MCG:N = 1:1 | 0.8 |
| | MCG:O = 1:1 | 0.4 |
| | MCG:DCG:N = 1:9:10 | 0.3 |
| | MCG:DCG:O = 1:1:2 | 0.2 |

TABLE 29

Minimum Growth Inhibitory Concentration (mg/l)

| Mill No. | Microbicidal Ingredient | MIC 24 Hr (mg/l) |
|---|---|---|
| V | MCG | 2.5 |
| | DCG | 3.0 |
| | F | 4.0 |
| | I | 4.0 |
| | MCG:DCG:F = 9:1:10 | 0.20 |
| | MCG:DCG:I = 1:1:2 | 0.35 |
| | MCG:F = 1:1 | 0.6 |
| | MCG:I = 1:1 | 0.6 |

Test Example 13: (Evaluation of Bacteriostatic Effect on White Water from Papermaking Mill (No.3))

Test water prepared in the test example 12 was used. Bouillon medium was added to the test water. The mixture was put to a previously sterilized L shaped test tube, to which a definite amount of microbicidal ingredient was added and shaken at 30° C. Then, the absorbance at 660 nm was measured every 1 hour. The time (t) from the initiation of the measurement until an increase in absorbance by growth of the microorganisms exceeded 0.1 was measured. The time T showing the inhibition of the growth of microbes is calculated by the formula as follows:

$$T = t_x - t_0$$

wherein $t_0$ is a time (t) when no ingredient is added and $t_x$ is a time (t) when x mg of ingredients are added.

The result is shown in Tables 30 to 33.

TABLE 30

| Mill No. | Amount X (mg/l) | Composition | Time T for inhibiting the growth of microbes (Hr) | | | | | | | | |
|---|---|---|---|---|---|---|---|---|---|---|---|
| | | | 1:0 | 20:1 | 10:1 | 5:1 | 3:1 | 1:3 | 1:5 | 1:10 | 0:1 |
| II | 0.4 | MCG:C | 4 | — | 10 | 22 | >24 | >24 | 18 | 9 | 2 |
| | | MCG:D | 4 | 8 | 18 | >24 | >24 | >24 | 21 | 5 | 3 |
| | 0.5 | MCG:W | 4 | 13 | 22 | >24 | >24 | >24 | 17 | 8 | 2 |

TABLE 31

| Mill No. | Amount X (mg/l) | Composition | Time T for inhibiting the growth of microbes (Hr) | | | | | | | | |
|---|---|---|---|---|---|---|---|---|---|---|---|
| | | | 1:0 | 20:1 | 5:1 | 3:1 | 1:3 | 1:5 | 1:10 | 1:20 | 0:1 |
| III | 2.0 | MCG:G | 3 | 5 | 17 | >24 | >24 | >24 | 10 | 3 | 0 |
| | | MCG:K | 3 | 9 | 18 | >24 | >24 | >24 | 16 | 5 | 0 |
| | | MCG:E | 3 | 6 | >24 | >24 | >24 | >24 | 9 | 1 | 0 |
| | | MCG:H | 3 | 4 | 10 | >24 | >24 | >24 | 18 | 4 | 0 |

TABLE 32

| Mill No. | Amount X (mg/l) | Composition | Time T for inhibiting the growth of microbes (Hr) | | | | | | | | |
|---|---|---|---|---|---|---|---|---|---|---|---|
| | | | 1:0 | 5:1 | 3:1 | 1:3 | 1:5 | 1:10 | 1:20 | 1:50 | 0:1 |
| IV | 1.0 | MCG:L | 4 | 10 | >24 | >24 | >24 | 20 | 10 | 6 | 2 |
| | | MCG:M | 4 | 10 | >24 | >24 | >24 | 20 | 10 | 6 | 2 |
| | | MCG:N | 4 | 12 | >24 | >24 | >24 | 22 | 13 | 6 | 3 |
| | | MCG:O | 4 | 1B | >24 | >24 | >24 | 22 | 15 | 6 | 2 |

TABLE 33

| Mill No. | Amount X (mg/l) | Composition | Time T for inhibiting the growth of microbes (Hr) | | | | | | | | |
|---|---|---|---|---|---|---|---|---|---|---|---|
| | | | 1:0 | 10:1 | 5:1 | 3:1 | 1:1 | 1:3 | 1:5 | 1:10 | 0:1 |
| V | 1.5 | MCG:F | 5 | 7 | 16 | >24 | >24 | >24 | 16 | 6 | 1 |
| | | MCG:I | 5 | 8 | 10 | >24 | >24 | >24 | 19 | 7 | 2 |

Test Example 14: (Evaluation of Microbicidal Effect on White Water from Papermaking Mill (No.2))

To white water sampled from a papermaking mill (IV), microbicidal ingredient was added at the amount of 2 mg/l and cultivated under shaking for 30 minutes at 30° C. (Paper: standard, pH: 7.3, $SO_3^{2-}$: 15 mg/l, viable cell number: $1.0 \times 10^7$ cfu/ml, microorganism: Pseudomonas, Flavobacterium, Alcaligenes and Bacillus species).

time T showing the inhibition of the growth of microbes is calculated by the formula as follows:

$$T = t_x - t_0$$

wherein $t_0$ is a time (t) when no ingredient is added and $t_x$ is a time (t) when x mg of ingredients are added.

The result is shown in Table 35.

TABLE 35

| Composition | Time T for inhibiting the growth of microbes (Hr) | | | | | | | |
|---|---|---|---|---|---|---|---|---|
| | 1:0 | 10:1 | 5:1 | 3:1 | 1:1 | 1:3 | 1:5 | 1:10 | 0:1 |
| MCG:P | 5 | 9 | 15 | >24 | >24 | >24 | 22 | 8 | 2 |
| MCG:Q | 5 | 9 | 15 | >24 | >24 | >24 | 20 | 6 | 1 |
| | Comparative | | | Example | | | | Comparative |

TABLE 34

| Ingredient | Number of viable cells |
|---|---|
| *Comparative* | |
| DCG | $1.8 \times 10^6$ |
| P | $3.1 \times 10^6$ |
| Q | $8.5 \times 10^6$ |
| *Example* | |
| MCG | $2.5 \times 10^4$ |
| MCG:P = 3:1 | $2 \times 10^2$ |
| MCG:P = 1:3 | $2.8 \times 10^3$ |
| MCG:Q = 3:1 | $5 \times 10^2$ |
| MCG:Q = 1:3 | $5.1 \times 10^3$ |
| MCG:DCG:P = 1:1:1 | $10^2$ or less |
| MCG:DCG:Q = 1:1:1 | $10^2$ or less |
| MCG:W = 1:3 | $1.9 \times 10^3$ |
| MCG:DCG:W = 1:1:1 | $10^2$ or less |

Test Example 15: (Evaluation of Bacteriostatic Effect on White Water from Papermaking Mill (No.1))

White water sampled from a papermaking mill (VII) was filtered through No. 2 filter paper to prepare test water (Paper: cardboard, pH: 6.0, $SO_3^{2-}$: 20 mg/l, viable cell number: $1.1 \times 10^8$ cfu/ml, microorganism: Pseudomonas, Flavobacterium, Alcaligenes and Bacillus species).

Bouillon medium was added to the test water. The mixture was put to a previously sterilized L shaped test tube, to which bacteriostatic ingredient in the amount of 1.5 mg/l was added and cultivated under shaking at 30° C. Then, the absorbance at 660 nm was measured every 1 hour. The time (t) from the initiation of the measurement until an increase in the absorbance by growth of the microorganisms exceeded 0.1 was measured. The Test Example 16: (Evaluation of Bacteriostatic Effect on White Water from Papermaking Mill (No.2))

White water sampled from a papermaking mill (VIII) was filtered through No. 2 filter paper to prepare test water (Paper: Newspaper, pH: 5.4, $SO_3^{2-}$: 10 mg/l, viable cell number: $1.1 \times 10^6$ cfu/ml, microorganism: Pseudomonas, Flavobacterium, Alcaligenes and Bacillus species).

Bouillon medium was added to the test water. The mixture was put to a previously sterilized L shaped test tube, to which microbicidal ingredient in the predetermined amount was added and cultivated under shaking at 30° C. After 24 hours, turbidity caused by the growth of microorganisms was measured by the absorbance at 660 nm whereupon the effect was judged.

The minimum amount whereby no increase in absorbance by addition of the ingredient was noted, i.e., minimum growth inhibitory concentration (MIC, 24 h) of the ingredients was measured.

The result is shown in Table 36.

TABLE 36

| Mill No. | Minimum Growth Inhibitory Concentration (mg/l) | |
|---|---|---|
| | Ingredient | MIC 24 Hr (mg/l) |
| VIII | MCG | 0.8 |
| | DCG | 1.0 |
| | R | 1.6 |
| | S | 1.6 |
| | T | 2.0 |
| | U | 2.0 |
| | V | 1.4 |
| | MCG:DCG:R = 1:9:10 | 0.10 |
| | MCG:DCG:S = 1:9:10 | 0.10 |
| | MCG:DCG:T = 9:1:10 | 0.15 |
| | MCG:DCG:U = 9:1:10 | 0.20 |
| | MCG:DCG:V = 1:9:10 | 0.10 |
| | MCG:R = 1:1 | 0.25 |

TABLE 36-continued

| Minimum Growth Inhibitory Concentration (mg/l) | | |
|---|---|---|
| Mill No. | Ingredient | MIC 24 Hr (mg/l) |
| | MCG:S = 1:1 | 0.35 |
| | MCG:T = 1:1 | 0.35 |
| | MCG:U = 1:1 | 0.35 |
| | MCG:V = 1:1 | 0.25 |

Test Example 17: (Evaluation for Bacteriostatic Effect on White Water from Papermaking Mill (No.4))

Test water prepared in the test example 15 was used.
Bouillon medium was added to the testing water. The resultant mixture was put to a previously sterilized L shaped test tube, to which bacteriostatic ingredient in the amount of 1.5 mg/l was added and cultivated under shaking at 30° C. Then, the absorbance at 660 nm was measured every 1 hour. The time (t) from the initiation of the measurement until an increase in the absorbance by growth of the microorganisms exceeded 0.1 was measured.

The time T showing the inhibition of the growth of microbes is calculated by the formula as follows:

$$T = t_x - t_0$$

wherein $t_0$ is a time (t) when no ingredient is added and $t_x$ is a time (t) when x mg of ingredients are added.
The result is shown in Table 37.

TABLE 37

| Mill No. | Amount X (mg/l) | Composition | Time T for inhibiting the growth of microbes (Hr) | | | | | | | | |
|---|---|---|---|---|---|---|---|---|---|---|---|
| | | | 1:0 | 20:1 | 10:1 | 5:1 | 3:1 | 1:3 | 1:5 | 1:10 | 0:1 |
| VIII | | MCG:R | 5 | 12 | 20 | >24 | >24 | >24 | >24 | 13 | 2 |
| | | MCG:S | 5 | 13 | 21 | >24 | >24 | >24 | >24 | 14 | 3 |
| | | MCG:T | 5 | 10 | 17 | >24 | >24 | >24 | >24 | 8 | 0 |
| | | MCG:U | 5 | 10 | 15 | >24 | >24 | >24 | >24 | 8 | 0 |
| | | MCG:V | 5 | 13 | 22 | >24 | >24 | >24 | >24 | 14 | 3 |

Test Example 18: (Evaluation of Bacteriostatic Effect on White Water from Papermaking Mill (No.3))

White water sampled from a papermaking mill and filtered through No.2 filter paper was used as test water (Paper: High quality paper (acidic paper), pH: 4.3, $SO_3^{2-}$: 0 mg/l, viable cell number: $5.0 \times 10^5$ cfu/ml, microorganism: Pseudomonas, Flavobacterium, Alcaligenes and Bacillus species).

Bouillon medium was added to the test water. The resultant mixture was put to a previously sterilized L shaped test tube, to which bacteriostatic ingredient in the predetermined amount was added and cultivated at 30° C. After 24 hours, the turbidity caused by the growth of microorganisms was judged.

The minimum amount whereby no increase in absorbance by the addition of the ingredients was noted, i.e., minimum inhibitory concentration (MIC, 24 hr) of the ingredient was measured.

The result is shown+in Table 38.

TABLE 38

| Minimum Growth Inhibitory Concentration (mg/l) | |
|---|---|
| Ingredient | MIC 24 Hr (mg/l) |
| MCG | 0.4 |
| W | 0.5 |
| MCG:W = 1:1 | 0.20 |
| MCG:DCG:W = 1:9:10 | 0.10 |

TABLE 38-continued

| Minimum Growth Inhibitory Concentration (mg/l) | |
|---|---|
| Ingredient | MIC 24 Hr (mg/l) |
| MCG:DCG:W = 9:1:10 | 0.10 |
| MCG:DCG:W = 1:1:1 | 0.05 |

Test Example 19: (Evaluation of Bacteriostatic Effect as a Slime Controlling Agent in Industrial Water System (No.2))

Slimes generated in sprinkle board and wall of hot water pit in open circulating cooling tower system were dispersed in an industrial water and filtered through No.2 filter paper to prepare test water (pH: 7.2, viable cell number: $2.0 \times 10^6$ cfu/ml, microorganisms: Pseudomonas, Flavobacterium, Alcaligenes and Bacillus).

Bouillon medium was added to the test water. The resultant mixture was put to a previously sterilized L shaped test tube. Next, microbicidal ingredient was added thereto and cultivated under shaking at 30° C. for 24 hours. Then, the turbidity caused by the growth of microorganisms was measured by an absorbance at 660 nm whereupon the effect was judged.

The minimum amount whereby no increase in absorbance by the addition of the ingredient was noted, i.e., minimum inhibitory concentration (MIC, 24 hr) of the ingredient was measured.

The result is shown in Table 39.

TABLE 39

| Minimum Growth Inhibitory Concentration (mg/l) | |
|---|---|
| Ingredient | MIC 24 Hr (mg/l) |
| DCG | 0.9 |
| C | 0.8 |
| D | 0.8 |
| H | 1.0 |
| Comparative example | |
| DCG:C = 1:1 | 0.3 |
| DCG:D = 1:1 | 0.3 |
| DCG:H = 1:1 | 0.4 |
| Example | |

Test Example 20: (Evaluation of Bacteriostatic Effect on White Water from Papermaking Mill (Part 5))

White water sampled from a papermaking mill (I) was filtered through No.2 filter paper to prepare test water (Paper: High quality paper (acidic paper), pH: 4.3, $SO_3^{2-}$: 0 mg/l, viable cell number: $5.0 \times 10^5$ cfu/ml, microorganisms: Pseudomonas, Flavobacterium, Alcaligenes and Bacillus).

Bouillon medium was added to the test water. The mixture was put to a previously sterilized L shaped test tube, to which bacteriostatic ingredient in the predetermined amount was added and cultivated under shaking at 30° C. After 24 hours, the turbidity caused by the growth of microbes was measured by the absorbance at 660 run whereupon the effect was judged.

The minimum amount whereby no increase in absorbance by the addition of the ingredient was noted, i.e., minimum inhibitory concentration (MIC, 24 hr) of the ingredient was measured.

The result is shown in Table 40.

TABLE 40

| Mill No. | Ingredient | MIC 24 Hr (mg/l) |
|---|---|---|
| | Minimum Growth Inhibitory Concentration (mg/l) | |
| I | DCG | 0.5 |
| | C | 0.7 |
| | D | 0.5 |
| | G | 2.0 |
| | Q | 0.5 |
| | W | 0.5 |
| | DCG:C = 1:1 | 0.20 |
| | DCG:D = 1:1 | 0.20 |
| | DCG:G = 1:1 | 0.25 |
| | DCG:Q = 1:1 | 0.15 |
| | DCG:W = 1:1 | 0.20 |

Test Example 21: (Evaluation of Bacteriostatic Effect on White Water from Papermaking Mills (No.6))

White water sampled from a papermaking mills (II to V) (See Table 25) was filtered through No.2 filter paper to prepare test water.

Bouillon medium was added to the test water. The mixture was put to a previously sterilized L shaped test tube, to which bacteriostatic ingredient in the predetermined amount was added and cultivated under shaking at 30° C. Then, the absorbance at 660 nm was measured every 1 hour. The time (t) from the initiation of the measurement until an increase in the absorbance by growth of the microorganisms exceeded 0.1 was measured.

The time T showing the inhibition of the growth of microbes is calculated by the formula as follows:

$$T = t_x - t_0$$

wherein $t_0$ is a time (t) when no ingredient is added and $t_x$ is a time (t) when x mg of ingredients are added.

The result is shown in Tables 41 to 44.

TABLE 41

| Mill No. | Amount X (mg/l) | Composition | Time T for inhibiting the growth of microbes (Hr) | | | | | | | | |
|---|---|---|---|---|---|---|---|---|---|---|---|
| | | | 1:0 | 20:1 | 10:1 | 5:1 | 3:1 | 1:3 | 1:5 | 1:10 | 1:20 | 0:1 |
| II | 0.5 | DCG:C | 2 | — | 8 | 20 | >24 | >24 | >24 | 10 | 5 | 2 |
| | | DCG:D | 2 | 5 | 15 | >24 | >24 | >24 | 20 | 5 | — | 3 |
| | | | Comparative | | | | Example | | | | | Comparative |

TABLE 42

| Mill No. | Amount X (mg/l) | Composition | Time T for inhibiting the growth of microbes (Hr) | | | | | | | | |
|---|---|---|---|---|---|---|---|---|---|---|---|
| | | | 1:0 | 20:1 | 10:1 | 5:1 | 3:1 | 1:3 | 1:5 | 1:10 | 1:20 | 0:1 |
| III | 2.0 | DCG:C | 2 | 4 | 15 | >24 | >24 | >24 | 18 | 10 | 3 | 0 |
| | | DCG:K | 2 | 8 | 16 | >24 | >24 | >24 | 22 | 15 | 5 | 0 |
| | | DCG:E | 2 | 5 | >24 | >24 | >24 | >24 | >24 | 8 | 1 | 0 |
| | | DCG:W | 2 | 11 | 20 | >24 | >24 | >24 | 18 | 9 | 6 | 2 |
| | | | Comparative | | | | Example | | | | | Comparative |

TABLE 43

| Mill No. | Amount X (mg/l) | Composition | Time T for inhibiting the growth of microbes (Hr) | | | | | | | |
|---|---|---|---|---|---|---|---|---|---|---|
| | | | 1:0 | 5:1 | 3:1 | 1:3 | 1:5 | 1:10 | 1:20 | 1:50 | 0:1 |
| IV | 1.0 | DCG:L | 3 | 8 | >24 | >24 | >24 | 18 | 9 | 5 | 2 |
| | | DCG:M | 3 | 8 | >24 | >24 | >24 | 18 | 9 | 5 | 2 |
| | | DCG:N | 3 | 10 | >24 | >24 | >24 | 20 | 10 | 5 | 3 |
| | | DCG:O | 3 | 15 | >24 | >24 | >24 | 22 | 12 | 5 | 2 |
| | | | Comparative | | | Example | | | | | Comparative |

TABLE 44

| Mill No. | Amount X (mg/l) | Composition | Time T for inhibiting the growth of microbes | | | | | | | | |
|---|---|---|---|---|---|---|---|---|---|---|---|
| | | | 1:0 | 10:1 | 5:1 | 3:1 | 1:1 | 1:3 | 1:5 | 1:10 | 0:1 |
| V | 1.5 | DCG:H | 4 | 6 | 14 | >24 | >24 | >24 | 12 | 5 | 1 |
| | | DCG:J | 5 | 7 | 13 | >24 | >24 | >24 | 18 | 6 | 1 |
| | | DCG:P | 4 | 8 | 15 | >24 | >24 | >24 | 20 | 7 | 2 |

Test Example 22: (Evaluation of Microbicidal Effect on White Water from Papermaking Mill (No.7))

To white water sampled from a papermaking mill (VI) (Paper: Standard, pH: 7.3, $SO_3^{2-}$: 15 mg/l, viable cell number: $1.0 \times 10^7$ cfu/ml, microorganisms: Pseudomonas, Flavobacterium, Alcaligenes and Bacillus), 2 mg/l of microbicidal ingredient was added and cultivated under shaking for 30 minutes at 30° C. Then the number of surviving cells was measured.

The result is shown in Table 45.

TABLE 45

| Ingredient | Viable cell number (cfu/ml) | Ingredient | Viable cell number (cfu/ml) |
|---|---|---|---|
| DCG | $1.8 \times 10^6$ | DCG:P = 3:1 | $5 \times 10^2$ |
| O | $3.1 \times 10^6$ | DCG:P = 1:3 | $4.1 \times 10^3$ |
| P | $8.5 \times 10^6$ | DCG:Q = 3:1 | $1.0 \times 10^3$ |
| W | $8.8 \times 10^5$ | DCG:Q = 1:3 | $6.5 \times 10^3$ |
| | | DCG:W = 3:1 | $1.1 \times 10^3$ |
| | | DCG:W = 1:3 | $3.9 \times 10^3$ |

Test Example 23: (Evaluation of Bacteriostatic Effect on White Water from Papermaking Mill (No.3))

White water sampled from a papermaking mill (VII) was filtered through filter paper No.2 to prepare test water (Paper: Newspaper, pH: 5.4, $SO_3^{2-}$: 10 mg/l, viable cell number: $1.0 \times 10^6$ cfu/ml, microorganisms: Pseudomonas, Flavobacterium, Alcaligenes and Bacillus).

Bouillon medium was added to the test water. The mixture was put to a previously sterilized L shaped test tube, to which bacteriostatic ingredient in the predetermined amount was added and cultivated under shaking at 30° C. After 24 hours, the turbidity caused by the growth of microorganisms was measured by the absorbance at 660 nm whereupon the microbicidal effect was judged.

The minimum amount whereby no increase in absorbance by the addition of the ingredients was noted, i.e., minimum inhibitory concentration (MIC, 24 hr) of the ingredient was measured.

The result is shown in Table 46.

Test Example 24: (Evaluation of Bacteriostatic Effect on White Water from Papermaking Mill (No.8))

White water sampled from a papermaking mill (VIII, for newspaper) was filtered through filter paper No.2 to prepare test water.

Bouillon medium was added to the test water. The mixture was put to a previously sterilized L shaped test tube, to which microbicidal ingredient in the predetermined amount was added and cultivated under shaking at 30° C. Then, the absorbance at 660 nm was measured every 1 hour. The time (t) from the initiation of the measurement until an increase in the absorbance by growth of the microorganisms exceeded 0.1 was measured.

The time T showing the inhibition of the growth of microbes is calculated by the formula as follows:

$$T = t_x - t_0$$

wherein $t_0$ is a time (t) when no ingredient is added and $t_x$ is a time (t) when x mg of ingredients are added.

The result is shown in Table 47.

TABLE 46

| Mill No. | Minimum Growth Inhibitory Concentration (mg/l) | | | |
|---|---|---|---|---|
| | Ingredient | MIC 24 Hr (mg/l) | Ingredient | MIC 24 Hr (mg/l) |
| VII | DCG | 1.0 | DCG:R = 1:1 | 0.30 |
| | R | 1.6 | DCG:S = 1:1 | 0.40 |
| | S | 1.6 | DCG:T = 1:1 | 0.40 |
| | T | 2.0 | DCG:U = 1:1 | 0.40 |
| | U | 2.0 | DCG:V = 1:1 | 0.30 |
| | V | 1.4 | | |

TABLE 47

| Mill No. | Amount X (mg/l) | Composition | Time T for inhibiting the growth of microbes (Hr) | | | | | | | | | |
|---|---|---|---|---|---|---|---|---|---|---|---|---|
| | | | 1:0 | 20:1 | 10:1 | 5:1 | 3:1 | 1:3 | 1:3 | 1:5 | 1:10 | 0:1 |
| VIII | 0.5 | DCG:R | 5 | 9 | 20 | >24 | >24 | >24 | >24 | >24 | 12 | 2 |
| | | DCG:S | 5 | 10 | 22 | >24 | >24 | >24 | >24 | >24 | 13 | 3 |
| | | DCG:T | 5 | 8 | 15 | >24 | >24 | >24 | >24 | >24 | 7 | 0 |
| | | DCG:U | 5 | 8 | 16 | >24 | >24 | >24 | >24 | >24 | 7 | 0 |
| | | DCG:V | 5 | 12 | 21 | >24 | >24 | >24 | >24 | >24 | 13 | 3 |

Test Example 25: (Evaluation of Microbicidal Effect (No.1))

To white water sampled from a certain papermaking mill (pH: 4.3, viable cell number: $3.8 \times 10^6$ cfu/ml, microorganism: mainly consisted of Pseudomonas, Flavobacterium, Alcaligenes and Bacillus species), Compound No.2, as a single microbicidal ingredient, and complex microbicidal ingredients of Compound No.2 and known microbicidal ingredients in the amount of 0.5 mg/l were respectively added and cultivated under shaking for 30 minutes at 30° C. Then, the number of surviving cells was counted.

The result is shown in Table 48.

TABLE 48

| | Ingredient | Viable cell number (cfu/ml) | | | |
|---|---|---|---|---|---|
| | | Ingredient only 5 mg/l | 10:1 composition of ingredient and Compd. 2 0.5 mg/l | 1:1 composition of ingredient and Compd. 2 0.5 mg/l | 1:10 composition of ingredient and Compd. 2 0.5 mg/l |
| DCGE | Compound 2 | $1.2 \times 10^6$ | — | — | — |
| C | Methylene-bis(thiocyanate) | $3.5 \times 10^6$ | $1.2 \times 10^5$ | $4.9 \times 10^4$ | $7.9 \times 10^4$ |
| D | 5-chloro-2-methyl-4-isothiazolin-3-one | $3.4 \times 10^6$ | $5.0 \times 10^5$ | $1.5 \times 10^4$ | $2.3 \times 10^5$ |
| E | α-chloro-benzaldoxime | $2.7 \times 10^6$ | $2.0 \times 10^4$ | $6.5 \times 10^3$ | $3.1 \times 10^4$ |
| G | 2,2-dibromo-3-nitrilopropion-amide | $2.2 \times 10^6$ | $4.3 \times 10^3$ | $2.3 \times 10^3$ | $8.0 \times 10^3$ |
| I | 2,2-dibromo-2-nitro-1-ethanol | $3.3 \times 10^6$ | $3.3 \times 10^5$ | $2.5 \times 10^4$ | $9.2 \times 10^4$ |
| K | 2-bromo-2-nitro-1,3-diacetoxy-propane | $3.1 \times 10^6$ | $8.8 \times 10^5$ | $7.8 \times 10^4$ | $3.2 \times 10^5$ |
| N | 1,4-bis(bromo- | $4.5 \times 10^6$ | $4.7 \times 10^4$ | $1.0 \times 10^5$ | $3.5 \times 10^5$ |

TABLE 48-continued

| | Ingredient | Ingredient only 5 mg/l | Viable cell number (cfu/ml) 10:1 composition of ingredient and Compd. 2 0.5 mg/l | 1:1 composition of ingredient and Compd. 2 0.5 mg/l | 1:10 composition of ingredient and Compd. 2 0.5 mg/l |
|---|---|---|---|---|---|
| | acetoxy)-2-butene | | | | |
| P | 5-chloro-2,4,6-trifluoroisophthalonitrile | $2.1 \times 10^6$ | $7.1 \times 10^5$ | $3.9 \times 10^4$ | $5.6 \times 10^5$ |
| W | 4,5-dichloro-1,2-dithiol-3-one | $1.9 \times 10^6$ | $6.8 \times 10^4$ | $2.6 \times 10^3$ | $1.9 \times 10^4$ |
| R | 3,3,4,4-tetra-chlorotetra-hydrothiophene-1,1-dioxide | $3.5 \times 10^6$ | $4.5 \times 10^5$ | $7.4 \times 10^4$ | $5.0 \times 10^5$ |
| S | β-bromo-β-nitrostyrene | $3.1 \times 10^6$ | $4.4 \times 10^5$ | $3.2 \times 10^4$ | $5.1 \times 10^5$ |
| H | 2-bromo-2-nitro-1,3-propanediol | $3.6 \times 10^6$ | $9.4 \times 10^5$ | $9.3 \times 10^4$ | $2.6 \times 10^5$ |

Test Example 26: (Evaluation of Microbicidal Effect (No.2))

The synergistic effect of Compound No.2, having the strongest microbicidal effect among dichloroglyoxime diacetate derivatives, and known microbicidal ingredients was evaluated.

To white water sampled from a certain papermaking mill (pH: 5.1, a reducing substance: 8 mg/l in term of $SO_3^{2-}$, initial viable cell number: $7.8 \times 10^5$ cfu/ml, microorganisms: mainly consisted of Pseudomonas, Bacillus, Flavobacterium and Staphylococcus), microbicidal ingredients were added and cultivated under shaking for 30 minutes at 37° C. Then, the number of surviving cells was counted.

The result is shown in Table 49.

TABLE 49

| | Ingredient | Ingredient only 5 mg/l | Viable cell number (cvf/ml) 10:1 composition of ingredient and Compd. 2 0.5 mg/l | 1:1 composition of ingredient and Compd. 2 0.5 mg/l | 1:10 composition of ingredient and Compd. 2 0.5 mg/l |
|---|---|---|---|---|---|
| DCGE | Compound 2 | $2.9 \times 10^5$ | — | — | — |
| C | Methylene-bis(thiocyanate) | $7.2 \times 10^5$ | $2.6 \times 10^5$ | $6.9 \times 10^4$ | $1.5 \times 10^5$ |
| D | 5-chloro-2-methyl-4-isothiazolin-3-one | $7.0 \times 10^5$ | $9.7 \times 10^4$ | $3.0 \times 10^4$ | $7.0 \times 10^5$ |
| E | α-chloro-benzaldoxime | $3.5 \times 10^5$ | $7.9 \times 10^4$ | $9.9 \times 10^3$ | $2.5 \times 10^4$ |
| G | 2,2-dibromo-3-nitrilopropion-amide | $4.5 \times 10^5$ | $6.0 \times 10^4$ | $6.2 \times 10^3$ | $6.5 \times 10^4$ |
| I | 2,2-dibromo-2-nitro-1-ethanol | $6.5 \times 10^5$ | $5.4 \times 10^4$ | $3.8 \times 10^4$ | $7.5 \times 10^4$ |
| K | 2-bromo-2-nitro-1,3-diacetoxy-propane | $4.9 \times 10^5$ | $3.3 \times 10^5$ | $5.3 \times 10^4$ | $6.5 \times 10^4$ |
| N | 1,4-bis-(bromo-acetoxy)-2-butene | $6.2 \times 10^5$ | $7.0 \times 10^4$ | $1.9 \times 10^5$ | $2.3 \times 10^5$ |
| P | 5-chloro-2,4,6-trifluoroisophthalonitrile | $3.4 \times 10^5$ | $8.2 \times 10^4$ | $3.0 \times 10^4$ | $1.9 \times 10^5$ |
| W | 4,5-dichloro-1,2-dithiol-3-one | $6.8 \times 10^5$ | $8.9 \times 10^4$ | $9.7 \times 10^3$ | $6.0 \times 10^4$ |
| R | 3,3,4,4-tetra-chlorotetra-hydrothiophene-1,1-dioxide | $5.4 \times 10^5$ | $7.6 \times 10^4$ | $2.5 \times 10^4$ | $6.3 \times 10^4$ |
| S | β-bromo-β-nitrostyrene | $4.1 \times 10^5$ | $8.0 \times 10^4$ | $3.1 \times 10^4$ | $5.4 \times 10^4$ |
| H | 2-bromo-2-nitro-1,3-propanediol | $6.8 \times 10^5$ | $8.9 \times 10^4$ | $5.3 \times 10^4$ | $6.5 \times 10^4$ |

What we claimed is:

1. An industrial microbicide which comprises:
    at least one haloglyoxime derivative of the formula (I):

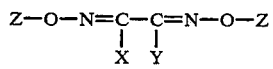

wherein X is a halogen atom; Y is a hydrogen atom, a halogen atom or a lower alkyl group having 1 to 4 carbon atoms; and Z is a hydrogen atom or an optionally halogenated lower alkanoyl group having 1 to 5 carbon atoms; and at least one known industrial microbicidal ingredient which is i) an organonitrogen-sulfur compound selected from the group consisting of methylenebisthiocyanate, 5-chloro-2-methyl-4-isothiazolin-3-one, 2-methyl-4-isothiazolin-3-one, and 4,5-dichloro-2-n-octyl-isothiazolin-3-one, ii) an organohalogen compound selected from the group consisting of 2-bromo-2-nitropropane-1,3-diol, 2-bromo-2-nitro-1-ethanol, 2,2-dibromo-2-nitro-1-ethanol, 2-bromo-2-nitro-1,3-diacetoxypropane, 2,2-dibromo-3-nitrilo-propionamide, β-bromo-β-nitrostyrene, 5-bromo-5-nitro-1,3-dioxane, 1,2-bis(bromoacetoxy)ethane, 1,2-bis(bromoacetoxy)propane, 1,4-bis(bromoacetoxy)-2-butene and 1,2,3,-tris(bromoacetoxy)propane, iii) an organonitrogen compound selected from the group consisting of α-chlorobenzaldoxime, 5-chloro-2,4,6-trifluoroisophthalonitrile and 5-chloro-2,4-difluoro-6-methoxyisophthalonitrile or iv) an organosulfur compound selected from the group consisting of 4,5-dichloro-1,2-dithiol-3-one, bis(trichloromethyl)sulfone and bis(tribromomethyl)sulfone, and optionally a carrier or diluent provided that the combination of monohaloglyoxime (Y and Z are hydrogen atoms) and the known industrial microbicidal ingredient is excluded.

2. An industrial microbicide according to claim 1, wherein the haloglyoxime derivative (I) is dihaloglyoxime.

3. An industrial microbicide according to claim 1, wherein the haloglyoxime derivative (I) is monoglyoxime and dihaloglyoxime.

4. An industrial microbicide according to claim 1, wherein the haloglyoxime derivative represented by formula (I) and the known industrial microbicidal ingredient are used in the ratio of 20:1 to 1:20 by weight.

5. A method for killing microbes for industrial use by adding a microbicidally effective amount of each of haloglyoxime derivative (I) as defined in claim 3 and a known industrial microbicidal ingredient simultaneously or separately to an industrial medium.

6. A method according to claim 5, wherein the haloglyoxime derivative (I) and the known industrial microbicidal ingredient are used in the ratio of 50:1 to 1:20 by weight and used in a medium at the concentration of 0.05 to 50 mg/l.

7. An industrial microbicide according to claim 1, wherein the halogen atom represented by X and/or Y is chlorine atom or bromine atom.

8. An industrial microbicide according to claim 1, wherein the haloglyoxime derivative (I) is a monohaloglyoxime.

9. An industrial microbicide according to claim 1, wherein in haloglyoxime derivative (I) is a dihaloglyoxime diacylate.

* * * * *